United States Patent
Zusman et al.

(10) Patent No.: US 6,588,279 B2
(45) Date of Patent: Jul. 8, 2003

(54) IMPACT TRANSMITTER FOR RECIPROCATING MACHINES

(75) Inventors: George Zusman, Houston, TX (US); Stephen M. Suarez, Houston, TX (US); Jon E. Palm, Houston, TX (US)

(73) Assignee: Metrix Instruments Co., Houston, TX (US)

( * ) Notice: Subject to any disclaimer, the term of this patent is extended or adjusted under 35 U.S.C. 154(b) by 27 days.

(21) Appl. No.: 10/025,930

(22) Filed: Dec. 18, 2001

(65) Prior Publication Data

US 2002/0078753 A1 Jun. 27, 2002

Related U.S. Application Data

(60) Provisional application No. 60/257,344, filed on Dec. 20, 2000.

(51) Int. Cl.[7] ............................................... G01H 11/06
(52) U.S. Cl. ......................................... 73/658; 340/683
(58) Field of Search .......................... 73/654, 658, 660; 340/683; 702/56

(56) References Cited

U.S. PATENT DOCUMENTS 3,733,596 A * 5/1973 Arima ........................ 340/518
3,822,586 A * 7/1974 Pollock ........................ 73/658
6,138,516 A * 10/2000 Tillman ........................ 340/683

\* cited by examiner

*Primary Examiner*—John E. Chapman
(74) *Attorney, Agent, or Firm*—Jackson Walker LLP; Clarence E. Eriksen; Bryan P. Galloway

(57) ABSTRACT

An apparatus for detecting and transmitting impact data is disclosed for use in monitoring early-stage development of harmful mechanical conditions for reciprocating machinery. The impact transmitter device includes a single self-contained unit having a stainless steel housing which contains an impact accelerometer, a detector circuit, a measurement and timing circuit, a 4–20 mA driver circuit, independent polarity circuit, and an electromagnetic impulse protection unit. The impact transmitter device further includes a field adjustable static threshold defining the severity of the impact detected, and a field adjustable reference time window interval. The variable severe impact level threshold allows an operator to isolate severe impacts from typical machine vibration. The variable time window interval allows an operator to synchronize the present invention with different machine speeds and to collect severe impact data over an appropriate time frame. Additionally, the impact transmitter device provides functionality independent of the polarity of the power of a programmable logic controller or distributed control system.

13 Claims, 3 Drawing Sheets

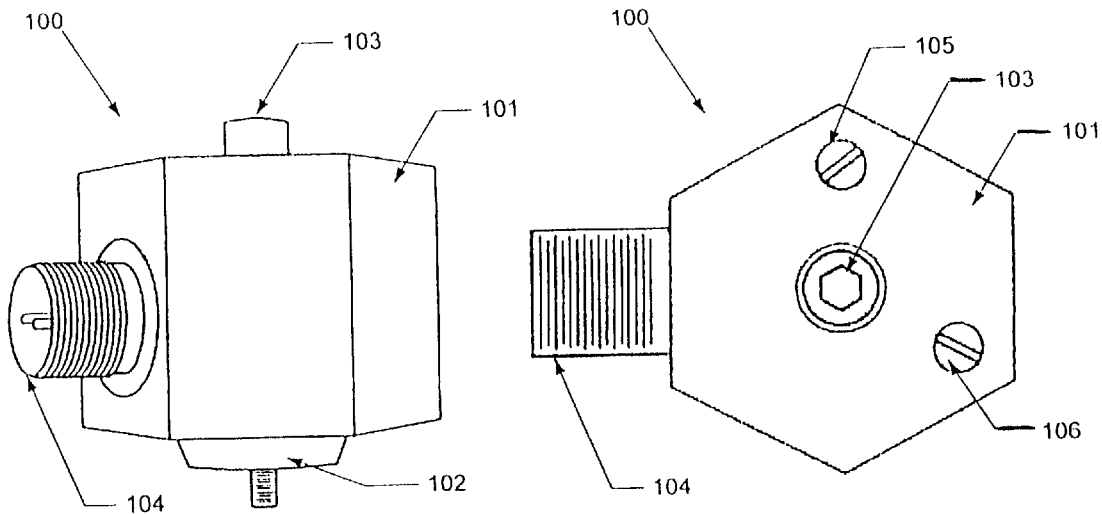
FIG. 1A
FIG. 1B
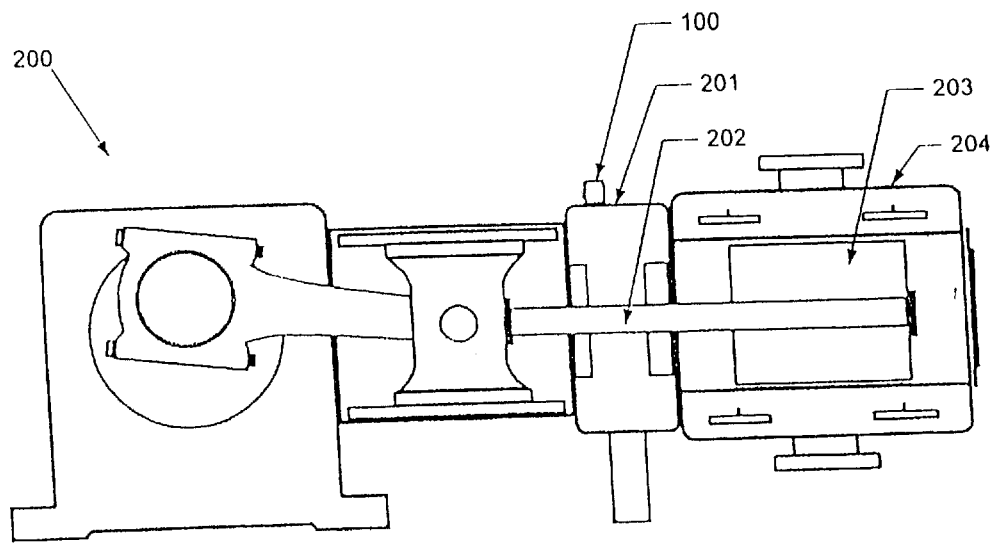
FIG. 2

IMPACT TRANSMITTER FOR RECIPROCATING MACHINES

CROSS-REFERENCE TO RELATED APPLICATIONS

The present application claims the benefit of the filing date of U.S. Provisional Patent Application Ser. No. 60/257, 344 filed Dec. 20, 2000.

BACKGROUND OF THE INVENTION

1. Field of the Invention

The present invention relates to an impact transmitting device which is used in impact monitoring operations. More particularly, the present invention relates to an apparatus for detecting and reporting mechanical impact events in reciprocating machines.

2. Description of the Prior Art

The principle of operation of an impact transmitting device for reciprocating machines is to detect free vibrations which are typically symptomatic of machine failure and to transmit the free vibration measurements in the form of an electrical signal. This electrical signal is received by an external logic solver which determines whether or not the reciprocating machine should be powered down. In practice, an impact transmitting device saves unnecessary waste caused by speculative preventative maintenance and increases the life-cycle of reciprocating machine components by alerting operators to early-stage development of harmful mechanical conditions. Such conditions may include loose rod nuts, loose bolts, excessive slipper clearance, worn pins, broken parts, liquid in the process, and rubbing.

In operation, an impact transmitting device is mounted to a reciprocating machine such as a reciprocating compressor having a compressor cylinder assembly. The impact transmitting device detects mechanical impact events in or near the compressor cylinder assembly. The amplitude of each detected impact event is compared to a preset threshold level. If the amplitude of the impact event surpasses the threshold, then the impact event is counted as an "above-threshold impact event." The number of above-threshold impact events that are counted by the impact transmitting device during a preset time window interval is reported to an external logic solver such as a programmable logic controller ("PLC") or distributed control system ("DCS"). The external logic solver compares the signal to a predetermined level of acceptable above-threshold impact events during the given time window. If the number of above-threshold level impact events is below the preset acceptable level, then the impact events are disregarded as a "nuisance alarm." However, if the number is at or above the acceptable level, then the machine is experiencing harmful mechanical events and must be shut down for appropriate maintenance.

While prior art impact transmitting devices offer the ability to detect and report useful mechanical impact data, it has been observed that these devices have at least two deficiencies. First, prior art impact transmitting devices are actually stand-alone rack mounted monitoring systems. As a result, prior art impact transmitting devices are expensive and cumbersome. Second, many prior art impact transmitting devices do not provide for manipulation of the impact threshold level or the time window interval during which the above-threshold impact events are counted. Moreover, the impact transmitter devices that do allow these parameters to be manipulated must be adjusted by using software prior to installation of the device or by an experienced technical person.

Accordingly, it would be desirable to have an impact transmitting device that functions as a single self-contained unit. Moreover, it would be desirable to have an impact transmitting device having a simple "field" adjustable impact threshold level for detecting above-threshold level impact events and a simple "field" adjustable time window interval during which these above-threshold level impact events are counted. These novel and useful results have been achieved by the present invention.

SUMMARY OF THE INVENTION

In accordance with the present invention, apparatus is provided for impact measurement and transmission for reciprocating machines.

An impact transmitting device in accordance with the present invention provides for the detection and transmission of (1) the quantity of severe impacts during a time window interval, and (2) the severity of the impacts above a static threshold. This impact quantity and severity measurement is used to differentiate singular "nuisance alarm" impacts from repeat "machine failure" impacts.

An impact transmitting device in accordance with the present invention further provides a single self-contained unit comprising a stainless steel housing which contains an impact accelerometer, a detector circuit, a measurement and timing circuit, a 4–20 mA driver circuit, independent polarity circuit, and an electromagnetic impulse protection unit.

An impact transmitting device in accordance with the present invention still further provides a field adjustable static threshold defining the severity of the impact, and a field adjustable reference time window interval. The variable severe impact level threshold allows an operator to isolate severe impacts from typical machine vibration. The variable time window interval allows an operator to synchronize the present invention with different machine speeds and to collect severe impact data over an appropriate time frame.

An impact transmitting device in accordance with the present invention also provides functionality independent of the polarity of the power of a PLC or DCS.

BRIEF DESCRIPTION OF THE DRAWINGS

In the accompanying drawings:

FIG. 1A is a side view of a preferred embodiment of the present invention illustrating a housing and a through-bolt used connect the housing to a reciprocating machine.

FIG. 1B is a plan view of a preferred embodiment of the present invention illustrating an adjustor to regulate impact threshold level and an adjustor to regulate time window interval.

FIG. 2 is a sectional view of a preferred embodiment of the present invention illustrating an impact transmitting device attached to a reciprocating compressor.

DESCRIPTION OF SPECIFIC EMBODIMENT

A detailed description of certain embodiments of the present invention is provided to facilitate an understanding of the invention. The detailed description is intended to illustrate particular embodiments of a method and apparatus for detection and transmission of impact signals for reciprocating machines. However, those skilled in the art who have the benefit of the present disclosure will envision other embodiments which do not depart from the scope of the present invention.

In this detailed description of a preferred embodiment of the present invention, the term "operatively connected" is used to mean "in direct connection with" or "in connection with via another element." Also, with respect to an electrical component having one or more inputs, the term "having an input" is understood to mean "having one or more inputs." Moreover, with respect to an electrical component having one or more outputs, the term "having an output" is understood to mean "having one or more outputs."

Figure 3:
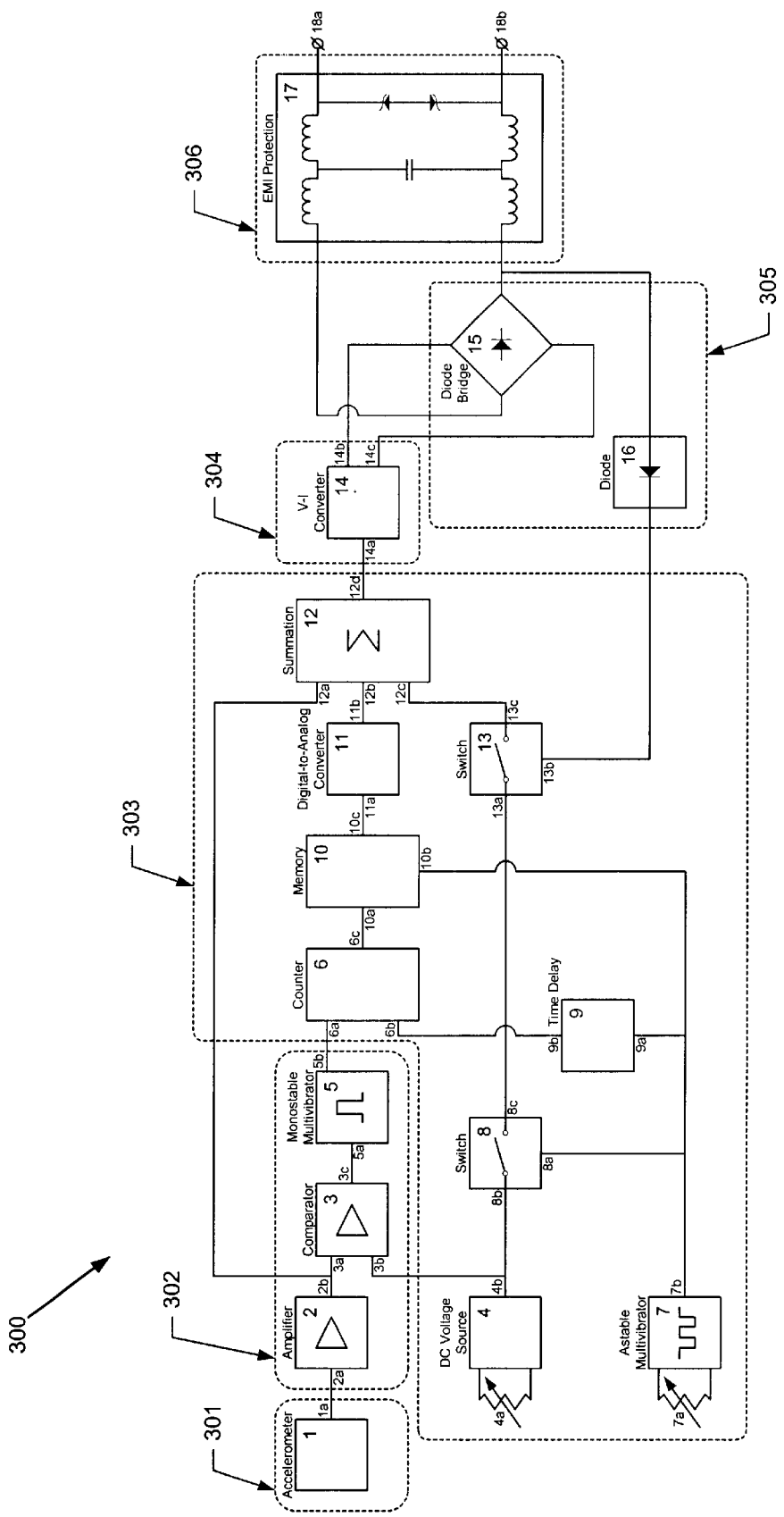
FIG. 3 is a schematic view of a preferred embodiment of the present invention illustrating electrical components and operating sequence.
Figure 4A:
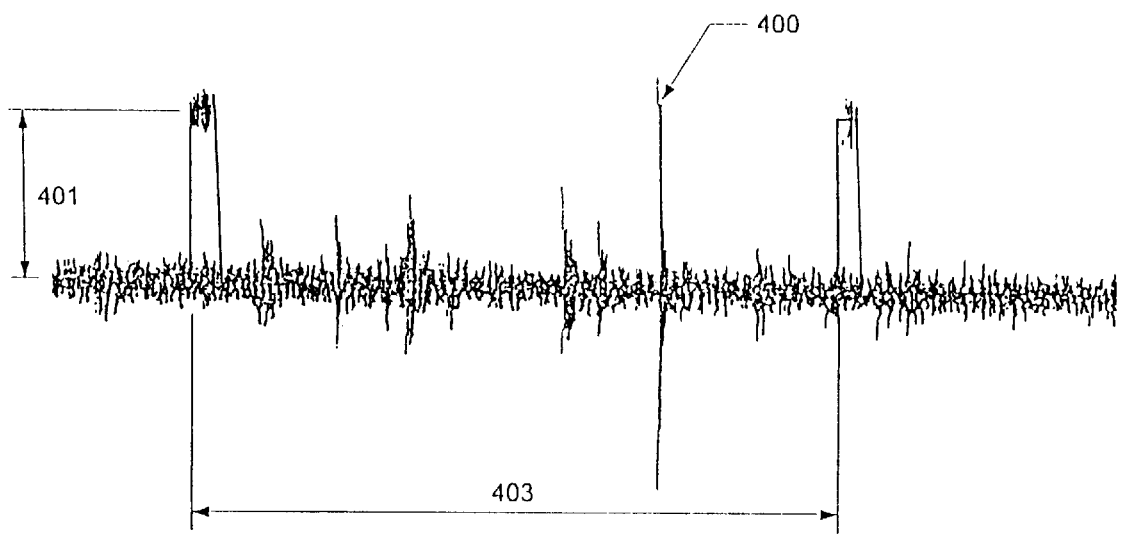
FIG. 4A is a representation of a mechanical vibration pattern.
Figure 4B:
FIG. 4B is a representation of impact pulses associated with the mechanical vibration pattern of FIG. 4A that are above an established impact threshold level.
Figure 4C:
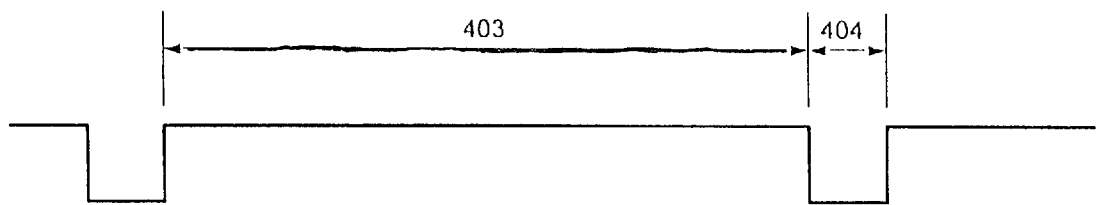
FIG. 4C is a representation of a time window interval associated with the mechanical vibration pattern of FIG. 4A.

With reference to FIGS. 1A and 1B, a particular embodiment of the present invention includes an impact transmitting device 100 comprising a stainless steel housing assembly 101, a mounting base 102, a through-bolt 103, an input connector 104, an impact level threshold adjustor 105, and a time window interval adjustor 106. The housing assembly 101 contains the impact transmitter detecting, measuring, and transmitting electrical unit 300 (FIG. 3). While the housing assembly 101 of the preferred embodiment of the present invention is fabricated from stainless steel, it is intended that the housing assembly can be fabricated from any durable material suitable for plant operating conditions.

With reference to FIG. 2, the through-bolt 103 is used to attach the mounting base 102 of the impact transmitting device 100 to a reciprocating compressor 200 having a cross-head 201 and a drive rod 202 moving a piston 203 through a cylinder 204. The impact transmitting device 100 is positioned on the cross-head 201 of the reciprocating compressor 200 such that the through-bolt 103 is perpendicular to the motion of the drive rod 202 and compressor piston 203 through the cylinder 204.

With reference to FIG. 3, the housing assembly 101 (FIG. 1A) contains a sensing unit 301, a detector circuit 302, a measurement and timing circuit 303, a 4–20 mA driver circuit 304, a independent polarity circuit 305, and an electromagnetic impulse protection unit 306.

The a sensing element 301 comprises a piezo-crystal accelerometer 1 having an output 1a. The detector circuit 302 comprises a charge amplifier 2 having an input 2a and an output 2b; a comparator 3 having inputs 3a and 3b and an output 3c; and a monostable multivibrator 5 having an input 5a and an output 5b. The measurement and timing circuit 303 comprises a DC reference voltage source 4 having a many-turn resistor 4a and an output 4b; a counter 6 having inputs 6a and 6b and an output 6c; an astable multivibrator 7 having a many-turn resistor 7a and an output 7b; a control switch 8 having inputs 8a and 8b and an output 8c; a time delay unit 9 having an input 9a and an output 9b; a digital memory 10 having write inputs 10a and 10b and an output 10c; a digital-to-analog converter 11 having an input 11a and an output 11b; a summation device 12 having inputs 12a, 12b, and 12c and an output 12d; and a control switch 13 having inputs 13a and 13b and an output 13c. The 4–20 mA driver circuit 304 comprises a voltage-to-current converter 14 having an input 14a and outputs 14b and 14c. The independent polarity circuit 305 comprises a diode bridge 15 and a diode 16. The electromagnetic protection unit 306 comprises protection unit 17, and terminals 18a and 18b.

With reference to FIGS. 3, 4A, 4B, and 4C, in operation, the piezo-crystal accelerometer 1 detects a free mechanical vibration force 400, or "impact." The output 1a of the piezo-crystal accelerometer 1 is connected to the input 2a of the charge amplifier 2. As the piezo-crystal accelerometer 1 is subjected to an impact, a voltage in proportion to the impact force ("impact-dependent voltage") is produced. The output 2b of the charge amplifier 2 is connected to the first input 3a of the comparator 3. The second input 3b of the comparator 3 is connected to the output 4b of the DC reference voltage source 4. The DC reference voltage source 4 is regulated by a multi-turn resistor 4a to establish a threshold voltage 401. If the impact-dependent voltage present at the first input 3a of the comparator 3 is less than the threshold voltage 401 from the DC reference voltage source 4, then the comparator 3 generates an output of "logic zero." However, if the impact-dependent voltage at the output 2b of the charge amplifier 2 exceeds the threshold voltage of the DC reference voltage source 4, then the output 3c of the comparator 3 is switched to "high level."

The output of the comparator 3 is connected to the input 5a of the monostable multivibrator 5. When the output 3c of the comparator 3 switches to "high level," the monostable multivibrator 5 generates a single output pulse 402, called an "event." The monostable multivibrator 5 is connected to the input 6a of the counter 6. The counter 6 counts the pulses received from the monostable multivibrator 5. This count represents the quantity of impacts producing voltage above the threshold established by the DC reference voltage source 4. The output 6c of the counter 6 is connected to the write input 10a of the digital memory 10.

The multi-turn resistor 7a of the astable multivibrator regulates a time window interval 403 during which each above-threshold impact events 402 is counted. The time window interval 403 is normally equal to the time required for 12 to 20 reciprocations of a reciprocating machine shaft to occur, which is equivalent to 0.3 to 4.0 seconds, and may be adjusted by the multi-turn resistor 7a.

The output 7b of the astable multivibrator 7 is connected to the input 8a of the control switch 8, to the input 9a of the time delay unit 9, and to the write input 10b of the digital memory 10. As the time window interval 403 reaches an end 404, the astable multivibrator 7 causes the digital memory 10 to store the quantity of events that were counted during the current time window interval. The counter 6 is then reset through the time delay unit 9.

The output 10c of the digital memory 10 is connected to the input 11a of the digital-to-analog convertor 11. The digital-to-analog converter 11 converts the digital value of the number of stored above-threshold impacts to an analog signal.

The output 11b of the digital-to-analog converter 11 is connected to the input 12b of the summation device 12. The output 12d of the summation device 12 is connected to the input 14a of the voltage-to-current convertor 14. The voltage-to-current converter 14 converts the voltage at the output 12d of summation device 12 to a current. The current produced by the voltage-to-current converter 14 is in direct proportion to the number of above-threshold impacts 400 that were detected and relayed as impact events 402 during the time window interval 403. The value of that current will range from 4 to 20 mA, where a current of 4 mA represents 0 events ("no impact") and a current of 20 mA represents 16 events. Each event is equivalent to 1 mA of current.

In addition to the DC 4–20 mA signal entering the summation device 12, the output 2b of the charge amplifier 2 is connected to the input 12a of the summation device to provide an AC signal which is proportional to the actual vibration level.

The outputs 14b and 14c of the voltage-to-current converter 14 are connected to the inputs 18a and 18b of the PLC or DCS (not shown) via the diode bridge 15 and the electromagnetic impulse protection unit 17. The diode bridge 15 allows the circuit 300 to function independent from the polarity established by the power supply of the PLC or DCS. The electromagnetic impulse protection unit 17 shields the circuit 300 from potentially damaging energy spikes.

The output of the DC reference voltage source 4 is connected to the input 8b of the switch 8. The output 8c of the switch 8 is connected to the input 13a of the switch 13. The output 13c of the switch 13 is connected to the input 12c of the summation device 12. The input 13b of switch 13 is operatively connected via the diode 16 to the voltage present on terminal 18b of the PLC or DCS. The switch 8 is closed during "time off" intervals 404 at the output 7b of the astable multivibrator 7. The switch 13 is closed when the polarity of the voltage on terminal 18b is positive. When the switch 13 is closed, impact threshold voltage and time window interval signals are included in the output 12d of the summation device 12.

With reference to FIG. 3, the independent polarity circuit 305 enables impact transmitter device to function independent of the polarity at the terminals 18a and 18b. Moreover, the field adjustments to the impact threshold level 401 and the time window interval 403 are accomplished by reversing the input connection 104 (FIGS. 1A and 1B) to terminals 18a and 18b. In this "reverse polarity" mode, the impact transmitter device will continue to function while an oscilloscope and a meter, or a combination scopemeter, is used to view the vibration data as the adjustments 105, 106 (FIG. 1B) are manipulated. While this reverse polarity mode is described with respect to an impact transmitter device, it is intended that a reverse polarity mode may be used to facilitate field adjustments of any 24 mA loop powered device—such as a vibration sensor.

The present invention provides a 4–20 mA loop powered impact transmitter device that is self-contained and enables an operator of the device to easily make field manipulations of the impact threshold level and the time window interval. These and other advantages of the present invention will be apparent to those skilled in the art.

What is claimed is:

1. Apparatus for detecting machine vibrations and transmitting machine vibration data to an external logic solver, said apparatus comprising a sensing element for sensing machine vibrations, a 4–20 mA driver circuit operatively connected to the sensing element for producing a current, and an independent polarity circuit operatively connected between the 4–20 mA driver circuit and the external logic solver to provide functionality that is independent of the polarity of the external logic solver.

2. The apparatus of claim 1, wherein said sensing element comprises an impact accelerometer.

3. The electrical apparatus of claim 1, wherein said sensing element comprises a vibration sensor.

4. An impact transmitter device for measuring impact events in a reciprocating machine and transmitting impact data to an external logic solver, said impact transmitting device comprising:

a housing assembly;

a two pin connector attached to the housing assembly for connecting the impact transmitter to the external logic solver;

means for mounting the housing assembly to the reciprocating machine; and an electrical unit residing within the housing and connected to the two pin connector for detecting and transmitting severity of machine impact events to the logic solver, said electrical unit comprising:

(i) an impact sensing element having an output, said impact sensing element for sensing the severity of each machine impact event in the reciprocating machine, (ii) a detector circuit having an input operatively connected to the output of the impact sensing element and an output, said detector circuit for producing a voltage in proportion to the severity of each impact event and producing a single output pulse for each impact event having a voltage greater than an adjustable reference voltage, (iii) a measurement and timing circuit having an input operatively connected to the output of the detector circuit and an output, said measurement and timing circuit for providing an adjustable reference voltage by which the voltage of each impact event is measured and an adjustable time window interval during which the output pulses of each impact event having a voltage greater than the reference voltage are counted and stored, (iv) a 4–20 mA driver circuit having an input operatively connected to the output of the measurement and timing circuit and an output, said 4–20 mA driver circuit for converting the voltage of the counted and stored output pulses to a proportional current between 4 mA and 20 mA, (v) an independent polarity circuit having an input operatively connected to the output of the 4–20 mA driver circuit and an output, said independent polarity circuit for providing functionality to the electrical unit that is independent of the polarity of the external logic solver, and (vi) two terminals operatively connected to the output of the independent polarity circuit, said two terminals for operatively connecting the electrical unit to the external logic solver.

5. The impact transmitter device of claim 4, wherein the electrical unit further comprises an electromagnetic impulse protection unit having an input operatively connected to the output of the independent polarity circuit and an output operatively connected to the two terminals, said electromagnetic impulse protection unit for protecting the electronic unit from electromagnetic energy surges.

6. The impact transmitting device of claim 4, wherein the impact sensing element comprises an impact accelerometer.

7. The impact transmitting device of claim 4, wherein the detector circuit comprises: (i) a charge amplifier having an input connected to the output of the impact sensing element and an output, said charge amplifier for producing the voltage in proportion to the severity of each machine impact event, (ii) a comparator having an input connected to both the output of the charge amplifier and the output of the measurement and timing circuit and an output, said comparator for comparing the voltage produced by the charge amplifier to the adjustable reference voltage provided by the measurement and timing circuit, and (iii) a monostable multivibrator having an input operatively connected to the output of the comparator and an output, said monostable multivibrator for producing the single output pulse for each impact event having a voltage greater than an adjustable reference voltage.

8. The impact transmitting device of claim 4, wherein the measurement and timing circuit comprises: (i) a DC reference voltage source having a many-turn resistor and an output operatively connected to the detector circuit, said DC reference voltage source for producing the adjustable reference voltage, (ii) an astable multivibrator having a many-turn resistor and an output, said astable multivibrator for regulating the time window interval, (iii) a time delay unit having an input operatively connected to the output of the astable multivibrator and an output, said time delay unit for providing a time period during which the output pulses are stored, (iv) a counter having an input operatively connected to both the output of the detector circuit and the output of the time delay unit and an output, said counter for counting the impact pulses produced by the detector circuit and producing a resultant digital number, (v) a digital memory having an input operatively connected to both the output of the counter and the output of the astable multivibrator and an output, said digital memory for storing the digital number of output pulses counted by the counter, (vi) a digital-to-analog converter having an input operatively connected to the output of the digital memory and an output, said digital-to-analog converter for converting the digital number stored in the digital memory to a corresponding analog signal, and (vii) a summation device having an input operatively connected to each of the outputs of the digital-to-analog converter, the DC reference voltage source, and the detector circuit and an output opertively connected to the 4–20 mA driver circuit, said summation device for providing the analog signal from the digital-to-analog converter, the reference voltage from the DC reference voltage source, and the voltage in proportion to the severity of each impact event from the detector circuit.

9. The impact transmitting device of claim 4, wherein the independent polarity circuit comprises: (i) a diode bridge operatively connected to the 4–20 mA driver circuit and to the two terminals, and (ii) a diode having an input operatively connected to the measurement and timing circuit and to one of the two terminals, said diode bridge and said diode for providing functionality to the electrical unit that is independent of the polarity of the external logic solver.

10. The impact transmitter device of claim 4, wherein the housing assembly is fabricated from stainless steel.

11. The impact transmitter device of claim 4, wherein the logic solver comprises a programmable logic controller.

12. The impact transmitter device of claim 4, wherein the logic solver comprises a distributed control system.

13. The impact transmitter device of claim 4, wherein the means for mounting the housing assembly to the reciprocating machine is a through-bolt connection.

* * * * *